US 6,644,306 B1

(12) United States Patent
Riebe et al.

(10) Patent No.: US 6,644,306 B1
(45) Date of Patent: Nov. 11, 2003

(54) VALVE FOR AEROSOL CONTAINER

(75) Inventors: Michael Thomas Riebe, Raleigh, NC (US); Mark Douglas Schulze, Wake Forest, NC (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/646,270

(22) PCT Filed: Mar. 17, 1999

(86) PCT No.: PCT/EP99/01757
§ 371 (c)(1),
(2), (4) Date: Sep. 15, 2000

(87) PCT Pub. No.: WO99/47195
PCT Pub. Date: Sep. 23, 1999

(30) Foreign Application Priority Data

Mar. 19, 1998 (GB) .............................. 9805938

(51) Int. Cl.[7] .............................. A61M 11/00
(52) U.S. Cl. .............................. 128/200.23; 128/200.14
(58) Field of Search ............... 128/200.23, 200.14, 128/203.15, 203.12, 203.23; 222/402.21

(56) References Cited

U.S. PATENT DOCUMENTS

| 2,886,217 A | * | 5/1959 | Thiel |
| 3,552,608 A | | 1/1971 | Sperry et al. |
| 3,658,214 A | | 4/1972 | Beard |
| 3,709,410 A | | 1/1973 | Cunningham |
| 4,418,846 A | | 12/1983 | Pong et al. |
| 4,693,799 A | | 9/1987 | Yanagihara et al. |
| 4,875,605 A | | 10/1989 | Weston |
| 4,902,318 A | * | 2/1990 | Stevens et al. ............... 55/270 |
| 4,961,966 A | * | 10/1990 | Stevens et al. ............. 427/299 |
| 5,027,986 A | | 7/1991 | Heinzel et al. |
| 5,147,075 A | | 9/1992 | Regan |
| 5,169,038 A | | 12/1992 | Di Giovanni |
| 5,421,492 A | * | 6/1995 | Barger et al. ............. 222/402.2 |
| 5,522,879 A | * | 6/1996 | Scopelianos .................... 623/1 |
| 5,575,311 A | * | 11/1996 | Kingsford ................. 137/625.5 |
| 5,772,085 A | | 6/1998 | Bryant et al. |
| 5,775,321 A | * | 7/1998 | Alband ................... 128/200.23 |
| 5,836,299 A | | 11/1998 | Kwon |
| 6,112,950 A | | 9/2000 | Di Giovanni et al. |
| 6,131,566 A | * | 10/2000 | Ashurst et al. ......... 128/200.14 |
| 6,143,277 A | * | 11/2000 | Ashurst et al. ............... 424/45 |
| 6,149,892 A | | 11/2000 | Britto |
| 6,253,762 B1 | * | 7/2001 | Britto .................... 128/200.14 |
| 6,318,603 B1 | * | 11/2001 | Burt ........................ 222/402.1 |
| 6,345,740 B1 | * | 2/2002 | Riebe ...................... 222/402.1 |

FOREIGN PATENT DOCUMENTS

| EP | 0 350 376 B1 | 1/1993 |
| FR | 2615124 | 12/1988 |
| FR | 2615173 | 12/1988 |
| FR | 2615172 | 1/1989 |
| FR | 2740527 A | 4/1997 |

(List continued on next page.)

OTHER PUBLICATIONS

Ratway, Robert J., et. al., "Surface Modification of Chlorobutyl Rubber by Plasma Polymerization," *Department of Materials Science and Engineering*, North Carolina State University, box 7907, Raleigh, NC 27695–7907, (Received Jun. 3, 1996; revised Feb. 21, 1997; accepted Feb. 25, 1997) pp. 1651 to 1660.

Ratway, Robert J., et. al., "Surface Modification of Nitrile Rubber by Plasma Polymerization," *Plasmas and Polymers*, vol. 3, No. 2, 1998, pp. 129–147.

(List continued on next page.)

*Primary Examiner*—Weilun Lo
*Assistant Examiner*—Darwin P. Erezo
(74) *Attorney, Agent, or Firm*—J. Michael Strickland

(57) ABSTRACT

The invention provides a valve for an aerosol container suitable for use in dispensing a quantity of the contents thereof. The valve components comprise a fluorinated polymer and/or a fluorinated coating which have been found to reduce drug deposition in the valve.

40 Claims, 1 Drawing Sheet

FOREIGN PATENT DOCUMENTS

Figure 1:
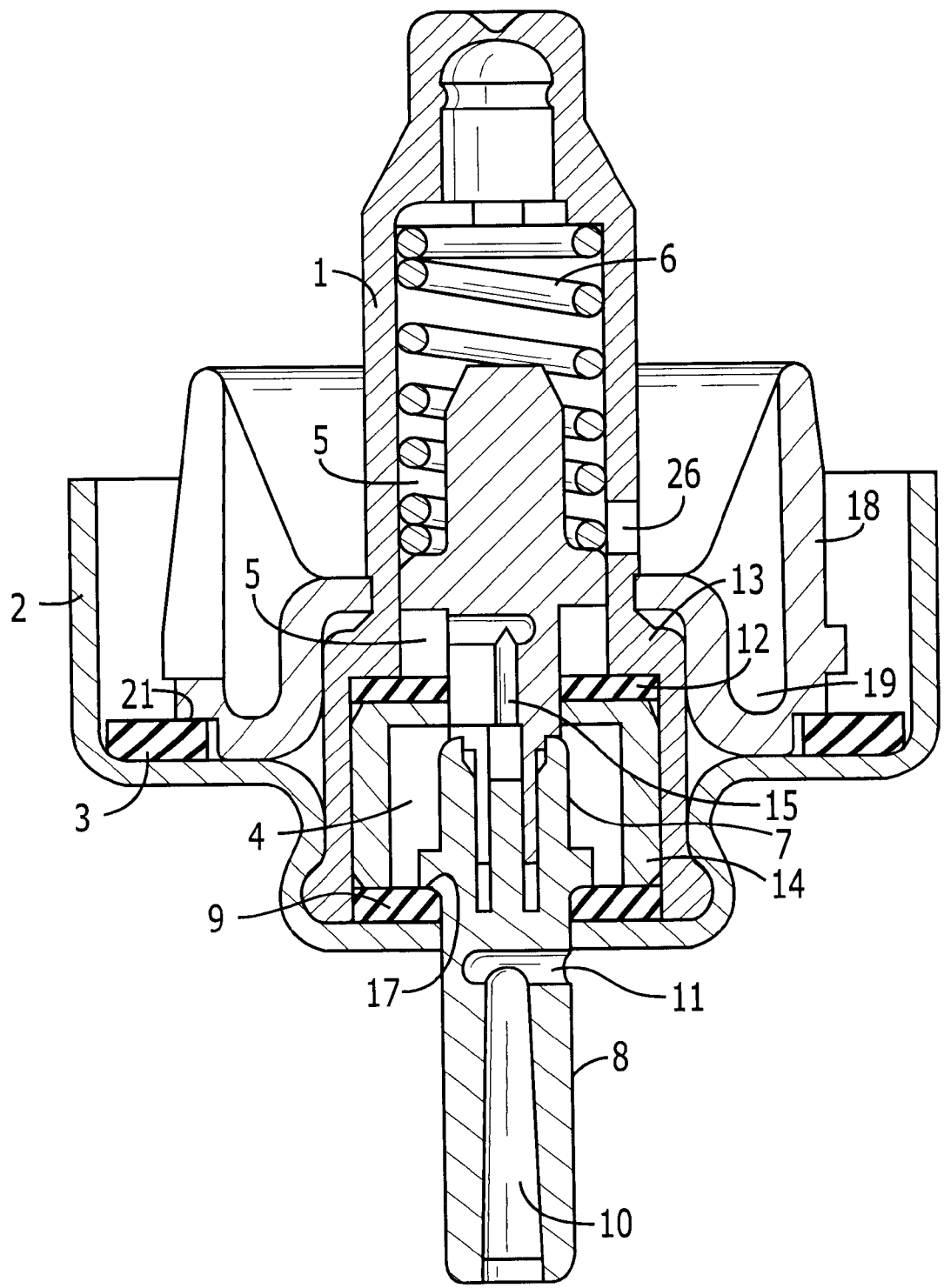

| | | |
|---|---|---|
| FR | 2740527 | 4/1997 |
| GB | 1227872 | 4/1971 |
| GB | 1227872 A | 4/1971 |
| GB | 2 328 932 A | 3/1999 |
| JP | 52-106383 | 3/1973 |
| WO | 96/32099 | 10/1996 |
| WO | Wo96 32099 A | 10/1996 |
| WO | 96/32344 | 10/1996 |
| WO | 97/09034 A | 3/1997 |
| WO | 97/16360 A | 5/1997 |
| WO | 98/35888 A | 8/1998 |
| WO | 99/06303 A | 2/1999 |
| WO | 99/42154 | 8/1999 |
| WO | 99/47195 | 9/1999 |

OTHER PUBLICATIONS

Patent Abstracts of Japan, vol. 018, No. 591 (C–1272), Nov. 11, 1994 & JP 06 220286A (Mitsubishi Cable Ind LTD), Aug. 9, 1994.

Database WPI, Section Ch, Week 7742, Derwent Publications Ltd., London, GB; Class A97, AN 77–74880Y XP002107403 & JP 52 106383 A (Toyo Aerosol Ind) Sep. 6, 1977.

* cited by examiner

VALVE FOR AEROSOL CONTAINER

This application is filed pursuant to 35 U.S.C. §371 as a United States National Phase Application of International Application No. PCT/EP99/01757 filed Mar. 17, 1999, which claims priority from GB9805938.9 filed Mar. 19, 1998.

The invention provides a valve for an aerosol container suitable for use in dispensing a quantity of the contents thereof and which may be used in the treatment of asthma and other ailments. In particular, the invention provides a valve for a metered dose inhaler suitable for use in dispensing metered doses of medicaments.

Containers for aerosol formulations commonly comprise a vial body (can) coupled to a valve. The valve comprises a valve stem through which the formulations are dispensed. Generally the valve includes a rubber valve seal intended to allow reciprocal movement of the valve stem which prevents leakage of propellant from the container. Metered dose inhalers comprise a valve which is designed to deliver a metered amount of an aerosol formulation to the recipient per actuation. Such a metering valve generally comprises a metering chamber which is of a set volume which aims to administer per actuation an accurate, predetermined dose.

Suitable valves for use in the invention are available from manufacturers well known in the aerosol industry, for example, from Valois, France (eg. DF10, DF30, DF60), Bespak plc, United Kingdom (eg. BK300, BK356, BK357) and 3M-Neotechnic Limited, United Kingdom (eg. Spraymiser™). The metering valves are used in association with commercially available canisters such as aluminum canisters, suitable for delivering pharmaceutical aerosol formulations.

Aerosol formulations which are generally used comprise a suspension of a medicament, one or more liquid propellants, optionally with a co-propellant, and optionally an adjuvant such as a solvent or a surfactant, though the invention may be applicable to the dispensing of any aerosol formulation. The aerosol formulation is under pressure in the canister.

It has been found that conventional aerosols, particularly metered dose inhalers, suffer impaired performance due to the deposition of drug particles in the valve component, particularly in the metering chamber. This leads to a high occurrence of inconsistency in the doses of drug being administered which becomes particularly acute over increasing numbers of actuations. The problem of drug deposition in conventional aerosols is particularly exacerbated when excipient-free aerosol formulations are used based on the hydrofluoro alkane (HFA) propellants 134a and 227. It has further been found that drug deposition increases with storage of the aerosol particularly when the aerosol is stored at high temperature and/or high humidity.

The invention provides a valve for an aerosol in which there is significantly reduced drug deposition compared with conventionally available valves when the valve is used in aerosols comprising an aerosol formulation for inhalation. In particular, the invention provides a metering valve having a metering chamber in which there is significantly reduced drug deposition.

Accordingly the invention relates to a valve for an aerosol container for dispensing a suspension or solution of a substance in a liquid propellant contained therein, wherein the valve comprises a valve body defining a chamber, a transfer passage through which a quantity of substance to be dispensed can pass from the container into the chamber, and dispensing means which allows the substance to be dispensed, in which the chamber comprises a fluorinated polymer.

The invention further provides an aerosol container which comprises a valve according to the invention, and an inhalation device, preferably a metered dose inhaler, which comprises the aerosol container.

The invention further provides a method of reducing drug deposition in a metering chamber for use in a metered dose inhaler by the use of a fluorinated polymer according to the invention.

The invention further provides a valve for an aerosol container as described hereinabove in which the surface of the chamber, for example, the metering chamber, in contact with the substance to be dispensed is coated with a fluorinated material including fluorine coatings, plastics materials comprising fluorinated materials etc.

The fluorinated coating is preferably a plasma coating, for example, a CF4 plasma coating. Preferably the fluorinated plasma coating CF4 is applied to the metering chamber of a metering valve which may be made from any conventionally used plastics material such as Acetal, polyester, etc. The plasma coating may consist of a fluorinated polymer laid down on the surface of the valve component, preferably the chamber, by polymerisation or direct modification of the material surface by interchange of hydrogen ions in the material with fluorine ions. The coating process typically takes place in a vacuum at ambient temperature. The components to be coated are placed inside a chamber which is evacuated. The fluorine monomer or fluorine source is introduced into the chamber at a controlled rate. The plasma is ignited within the chamber and maintained for a given time at a chosen power setting. At the end of the treatment the plasma is extinguished, the chamber flushed and the products retrieved. In the polymerisation process, a thin layer of plasma polymer will be bonded to the surface of the chamber, preferably a metering chamber, or any other surface of the valve to be coated.

The fluorinated polymer may be selected from any conventionally used fluorinated polymer/copolymer or mixtures thereof or mixture of the fluorinated polymer in combination with non-fluorinated polymers conventionally used in the manufacture of valves, such as acetal, polyester (PBT) as well as polymer blends with, for example, stainless steel (eg. PBT/stainless steel blend (PDX WO96082)), etc. Examples of suitable fluorinated polymers include polytetrafluoroethylene (PTFE), ethylenetetrafluoroethylene (ETFE), polyvinyldienefluoride (PVDF), perfluoroalkoxyalkane (PFA), polyvinylfluoride (PVF), polychlorotrirluoroethylene (PCTFE), fluorinated ethylenepropylene (FEP) etc. Suitable copolymers include copolymers of tetrafluoroethylene (TFE) with PFA, TFE with hexafluoropropylene (HFP) (available as FEP 6107 and FEP 100 from DYNEON), VDF with HFP (commercially available as Viton A), TFE with perfluoro(propyl vinyl ether) (available as PFA 6515N from DYNEON), a blend of TFE, hexafluoropropylene and vinylidene fluoride (available commercially as THV 200G from DYNEON), etc.

It should be noted, however, that any conventionally available polymer, copolymer or mixture thereof which comprises a fluorinated polymer and which can be used to make the valve for use in an inhaler according to the invention will be suitable. Examples of mixtures of polymers and/or copolymers comprise, for example, up to 80% by weight fluorinated polymer, optionally up to 40% by weight fluorinated polymer, optionally up to 20% by weight fluorinated polymer or optionally up to 5% by weight of fluorinated polymer. Preferably, fluorinated polymers selected from PTFE, PVF and PCTFE are used as mixtures with non-fluorinated polymers. For example a suitable material is HOSTAFORM X329™ (Hoechst) which is a 5% PTFE/Acetal blend, HOSTAFORM C9021TF which is a 20% PTFE/Acetal blend, PTFE/PBT blends (for example, LNP WL4040), PTFE/PBT/silicone blends (for example, LNP WL4540).

The fluorinated polymers and mixtures thereof used in the invention can be moulded in any conventional manner, for example, by injection moulding, plastic moulding etc.

According to a preferred embodiment of the invention, the valve is a metering valve comprising a metering chamber, a transfer passage through which a quantity of substance to be dispensed can pass from the container into the metering chamber, wherein in the first position the dispensing passage is isolated from the metering chamber and the metering chamber is in communication with the container via the transfer passage, and in the second position the dispensing passage is in communication with the metering chamber and the transfer passage is isolated from the metering chamber.

Medicaments which may be administered in the aerosol formulations, suitably suspended in a liquid propellant, include any drugs useful in inhalation therapy which may be present in a form which is substantially completely insoluble in the selected propellant system The aerosol formulation, if desired, may comprise one or more active ingredients. Aerosols comprising two active ingredients in a conventional propellant system are known for the treatment of respiratory disorders such as asthma. Appropriate medicaments may thus be selected from, for example, analgesics, e.g. codeine, dihydromorphine, ergotamine, fentanyl or morphine; anginal preparations, e.g. dilitiazem; antiallergics, e.g. cromolyn, cromoglycate or nedocromil; antibiotics, e.g. cephalosporins, penicillins, streptomycin, sulphonamides or tetracyclines; antihistamines, e.g. methapyrilene; anti-inflammatories, e.g. beclomethasone, flunisolide, fluticasone, tipredane, budesonide, triamcinolone acetonide; antitussives, e.g. noscapine; bronchodilators, e.g. ephedrine, epinephrine, fenoterol formoterol isoprenaline, isoproterenol, metaproternol phenylephrine, phenylpropanolamine, pirbuterol repoterol, rimiterol salbutamol, salmeterol, terbutaline or (-)-4-amino-3,4-dichloro-α-[[[6-[2-(2-pyridinyl)ethoxy]hexyl]amino] methyl]benzenemethanol; diuretics, e.g. amiloride; anticholinergics e.g. ipratropium bromide; hormones, e.g. cortisone, hydrocortisone or prednisolone; and therapeutic proteins and peptides, e.g. glucagon or insulin. It will be clear to a person skilled in the art that, where appropriate, the medicaments will be used in the form of salts (e.g. as alkali metal or amine salts or as acid addition salts) or as esters (e.g. lower alkyl esters) or as solvates (eg hydrates) to optimise the activity and/or stability of the medicament and/or to minimise the solubility of the medicament in the propellant.

Preferably the medicament is selected from bronchodilators and anti-inflammatory steroids of use in the treatment of asthma by inhalation therapy, including salbutamol (e.g. as the sulphate), salmeterol (e.g. as the hydroxynaphthoate known as salmeterol xinafoate), beclomethasone dipropionate or a ate thereof, fluticasone propionate or (-)4-amino-3,5-dichloro-α-[[[6-[2-(pyridinyl)ethoxy]hexyl]amino] methyl]benzenemethanol and mixtures thereof.

The particle size of the particulate medicament should be such as to permit inhalation of substantially all of the medicament into the lungs upon administration of the aerosol formulation and will thus desirably be less than 20 microns, preferably in the range 1 to 10 microns, e.g. 1 to 5 microns. The particle size of the medicament or the medicament together with the excipient may be reduced by conventional means, for example by milling, micronisation, spray-drying or controlled recrystallization.

The final aerosol formulation desirably contains 0.0005–10% w/w, preferably 0.0005–5% w/w, especially 0.01–1.0% w/w, of medicament relative to the total weight of the formulation.

Examples of aerosol propellants for the aerosol formulations include $CCl_3F$ (propellant 11) in admixture with $CCl_2F_2$ (propellant 12) $CF_2Cl.CF_2Cl$ (propellant 14), however, due to the ozone-depleting effects believed to be associated with such propellants, the valve for an aerosol container of the invention is more suitably used with aerosol formulations which comprise so called "ozone-friendly" propellants.

Preferably, the propellants are selected from hydrogen-containing chlorofluorocarbons and fluorocarbons and a number of medicinal aerosol formulations using such propellant systems have been disclosed m, for example, EP 0372777, WO91/04011, WO91/11173, WO91/11495, WO91/14422, WO92/00061, WO92/00062 and WO92/00107.

Suitable propellants include, for example, $C_{1-4}$ hydrogen-containing chlorofluorocarbons such as $CH_2ClF$, $CClF_2CHClF$, $CF_3CHClF$, $CHF_2CClF_2$, $CHClFCHF_2$, $CF_3CH_2Cl$ and $CClF2CH_3$; $C_{1-4}$ hydrogen-containing fluorocarbons such as $CHF_2CHF_2$, $CF_3CH_2F$, $CHF_2CH_3$ and $CF_3CHFCF_3$ and $C_{1-4}$ perfluorocarbons such as $CF_3CF_3$ and $CF_3CF_2CF_3$.

Where mixtures of the fluorocarbons or hydrogen-containing chlorofluorocarbons are employed they may be mixtures of the above identified compounds or mixtures, preferably binary mixtures, with other fluorocarbons or hydrogen-containing chlorofluorocarbons for example $CHClF_2$, $CH_2F_2$ and $CF_3CH_3$.

A single fluorocarbon or hydrogen-containing chlorofluorocarbon may be employed as the propellant. Particularly preferred as propellants are hydrogen-containing fluorocarbons, especially 1,1,1,2-tetrafluoroethane ($CF_3CH_2F$) (propellant 134a) and 1,1,1,2,3,3,3-heptafluoro-n-propane ($CF_3CHFCF_3$) (propellant 227) or a mixture thereof The propellants are preferably used in the absence of excipients and adjuvants, such as solvents and surfactants. As used herein "substantially free" refers to formulations which contain no significant amounts of surfactant, for example, less than 0.0001% by weight based upon the weight of the medicament. However, the invention also applies to formulations which include any conventionally used excipients, such as, surfactants etc.

The formulations may be prepared by any conventionally known process, for example, by dispersal of the medicament in the selected propellant in an appropriate container, e.g. with the aid of sonication.

Minimising and preferably avoiding the use of formulation excipients e.g. surfactants, cosolvents etc. in the aerosol formulations is advantageous since the formulations may be substantially taste and odour free, less irritant and less toxic than conventional formulations.

However, such formulations are associated with a higher degree of drug deposition on the valve components. The fluorinated valve according to the invention, particularly the valve having a fluorinated metering chamber, is preferably used to administer formulations substantially free of excipients which has been found to substantially reduce drug deposition in the valve.

The formulations may be filled into canisters suitable for delivering pharmaceutical aerosol formulations. Canisters generally comprise a container capable of withstanding the vapour pressure of the propellant used such as a plastic or plastic-coated glass bottle or preferably a metal can, for example an aluminium can which may optionally be anodised, lacquer- or polymer-coated and/or plastic-coated, which container is closed with a valve according to the invention.

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The medicament is added to a charge vessel and liquified propellant is pressure filled through the charge vessel into a manufacturing vessel. The drug suspension is mixed before recirculation to a filling machine and an aliquot of the drug suspension is then filled through the metering valve into the canister. Typically, in batches prepared for pharmaceutical use, each filled canister is check-weighed, coded with a batch number and packed into a tray for storage before release testing.

Each filled canister may be conveniently fitted into a suitable channelling device prior to use to form a metered dose inhaler for administration of the medicament into the lungs or nasal cavity of a patient. Suitable channelling devices comprise for example a valve actuator and a cylindrical or cone-like passage through which medicament may be delivered from the filled canister via the metering valve to the nose or mouth of a patient e.g. a mouthpiece actuator. A spacer may be placed between the passage and the mouthpiece. Metered dose inhalers are designed to deliver a fixed unit dosage of medicament per actuation or "puff", for example in the range of 10 to 5000 microgram medicament per puff According to a further embodiment of the invention, other parts of the inhaler which are also susceptible to drug deposition may comprise the fluorinated polymer of the invention and/or be coated with the fluorinated material according to the invention, for example, the actuator into which the filled canister comprising the valve is fitted for application by the patient. All or part of the actuator, for example, the valve actuator, mouthpiece actuator etc. may comprise the fluorinated polymer/copolymer or mixtures thereof and/or be coated with the fluorinated material.

Administration of medicament may be indicated for the treatment of mild, moderate or severe acute or chronic symptoms or for prophylactic treatment. It will be appreciated that the precise dose administered will depend on the age and condition of the patient, the particular particulate medicament used and the frequency of administration will ultimately be at the discretion of the attendant physician. When combinations of medicaments are employed the dose of each component of the combination will in general be that employed for each component when used alone. Typically, administration may be one or more times, for example from 1 to 8 times per day, giving for example 1,2,3 or 4 puffs each time.

Each valve actuation, for example, may deliver 25 $\mu$g, 50 $\mu$g, 100 $\mu$g, 200 $\mu$g or 250 $\mu$g of a medicament. Typically each filled canister for use in a metered dose inhaler contains 60, 100, 120 or 200 metered doses or puffs of medicament.

The invention will now be described further with reference to the accompanying drawing in which FIG. 1 is a section through a metering valve according to the invention and to the following Examples which serve to illustrate the invention but are not intended to be limiting.

A valve according to the invention is shown in FIG. 1 and comprises a valve body 1 sealed in a ferrule 2 by means of crimping, the ferrule itself being set on the neck of a container (not shown) with interposition of a gasket 3 in a well-known manner.

The valve body 1 is formed at its lower part with a metering chamber 4, and it upper part with a sampling chamber 5 which also acts as a housing for a return spring 6. The metering chamber is made at least in part from a fluorinated polymer and/or a fluorinated coating according to the invention. The words "upper" and "lower" are used for the container when it is in a use orientation with the neck of the container and valve at the lower end of the container which corresponds to the orientation of the valve as shown in FIG. 1. Inside the valve body 1 is disposed a valve stem 7, a part 8 of which extends outside the valve through lower stem seal 9 and ferrule 2. The stem part 8 is formed with an inner axial or longitudinal canal 10 opening at the outer end of the stem and in communication with a radial passage 11. The upper portion of stem 7 has a diameter such that it can slide through an opening in an upper stem seal 12 and will engage the periphery of that opening sufficiently to provide a seal. Upper stem seal 12 is held in position against a step 13 formed in the valve body 1 between the said lower and upper parts by a sleeve 14 which defines the metering chamber 4 between lower stem seal 9 and upper stem seal 12. The valve stem 7 has a passage 15 which, when the stem is in the inoperative position shown, provides a communication between the metering chamber 4 and sampling chamber 5, which itself communicates with the interior of the container via orifice 26 formed in the side of the valve body 1.

Valve stem 7 is biased downwardly to the inoperative position by return spring 6 and is provided with a shoulder 17 which abuts against lower stem seal 9. In the inoperative position as shown in FIG. 1 shoulder 17 abuts against lower stem seal 9 and radial passage 11 opens below lower stem seal 9 so that the metering chamber 4 is isolated from canal 10 and suspension inside cannot escape.

A ring 18 having a "U" shaped cross section extending in a radial direction is disposed around the valve body below orifice 26 so as to form a trough 19 around the valve body. As seen in FIG. 1 the ring is formed as a separate component having an inner annular contacting rim of a diameter suitable to provide a friction fit over the upper part of valve body 1, the ring seating against step 13 below the orifice 26. However, the ring 18 may alternatively be formed as an integrally moulded part of valve body 1.

To use the device the container is first shaken to homogenise the suspension within the container. The user then depresses the valve stem 7 against the force of the spring 6. When the valve stem is depressed both ends of the passage 15 come to lie on the side of upper stem seal 12 remote from the metering chamber 4. Thus a dose is metered within the fluorinated metering chamber. Continued depression of the valve stem will move the radial passage 11 into the metering chamber 4 while the upper stem seal 12 seals against the valve stem body. Thus, the metered dose can exit through the radial passage 11 and the outlet canal 10.

Releasing the valve stem causes it to return to the illustrated position under the force of the spring 6. The passage 15 then once again provides communication between the metering chamber 4 and sampling chamber 6. Accordingly, at this stage liquid passes under pressure from the container through orifice 26, through the passage 15 and thence into the metering chamber 4 to fill it.

In the following Examples each aerosol contains a suspension of a medicament in an excipient-free propellant formulation. In each case aerosols having conventionally available valves made from acetal or polyester are compared with aerosols having valves according to the invention in which either the metering chamber is made from fluorinated ethylene polymer or from polyester which has been plasma coated with CF4. In each case, the drug deposition generated through use is measured and "Dose Through Use" collection regimes are carried out to analyze doses administered during the life of the inhaler. The formulation tested in each case was an excipient-free propellant formulation comprising fluticasone propionate and 134a propellant.

Valve Drug Deposition Method

The quantity of drug deposited in the valve was measured. The interior valve components include the metering chamber, upper stem gasket and the parts of the upper and lower stem, which are within the metering chamber. For deposition performed at the beginning of use (BOU) of the inhaler, 2 testfire and 3 manual actuations are taken valve-down followed by 1 manual actuation valve-up to evacuate the metering chamber. Deposition performed on inhalers at end of use (EOU) has used 120 actuation inhalers. Before deposition is performed on these inhalers, 1 manual actuation valve-down is taken followed by 1 manual actuation valve-up to evacuate the metering chamber.

The sample preparation for measuring the valve deposition is the same for both BOU and EOU inhalers. Firstly, the valve stem is washed with acetonitrile. Then, the inhaler is chilled for five minutes in a bath of dry ice and methanol. The valve is removed from the inhaler and the valve interior components are washed quantitatively with acetonitrile into a 50 ml volumetric flask containing 25 ml water. The drug solution was made to volume and the resultant solution assayed for fluticasone propionate by HPLC.

Dosing Method

The following method was used to evaluate the dosing for the different valve variants for each experiment. The dose was collected as pairs of actuations at the BOU and EOU of the inhaler.

Before the dose collection at BOU, 2 testfire and 4 manual actuations were fired to waste valve-down. Actuations 1 and 2 were fired into a dose trap. The dose trap was washed quantitatively with acetonitrile into a 100 ml volumetric flask containing 50 ml water. The drug solution was made to volume and the resultant solution assayed for fluticasone propionate by HPLC.

After BOU collections, the inhalers have another 116 actuation fired to waste. The inhalers are at EOU. Actuations 119 and 120 were fired into a dose trap. The dose trap was washed quantitatively with acetonitrile into a 100 ml volumetric flask containing 50 ml water. The drug solution was made to volume and the resultant solution assayed for fluticasone propionate by HPLC.

EXAMPLE 1

The EOU interior valve deposition and dosing profile on valves was investigated with different polymer metering chambers. Fluticasone Propionate/Propellant HFA134a Inhalers, 50 microgram, 120 actuation were manufactured using the DF60 valve (acetal components, different polymer metering chambers and nylon ring). The inhalers were stored for a minimum of 2 weeks before analysis of the drug deposited on valve. The deposition and dosing data are presented in Tables 1 and 2.

TABLE 1

Drug deposition in metering chamber

| Composition of Metering Chamber | Amount of drug deposition - mg |
|---|---|
| Standard acetal | 0.26 |
| Standard polyester | 0.28 |
| CF4 coated polyester | 0.15 |
| FEP 100 | 0.10 |
| X329 (5% PTFE/acetal blend) | 0.18 |

TABLE 2

Dosing Data at Actuations 1 + 2/ 119 + 120 (for a 120 dose product)

| Composition of Metering Chamber | Actuation 1 + 2 Dose μg | SD | Actuation 119 + 120 Dose μg | SD | Increase in dose during life of inhaler (μg) |
|---|---|---|---|---|---|
| Standard acetal | 39.6 | 5% | 54.0 | 12.2% | 14.4 |
| Standard polyester | 37.7 | 3.4% | 52.3 | 7.1% | 14.6 |
| CF4 coated polyester | 41.0 | 1.6% | 49.6 | 7.5% | 8.6 |
| FEP 100 | 39.0 | 3.2% | 48.1 | 6.8% | 9.1 |

SD = Standard deviation

Table 2 demonstrates the improvement in the consistency of each dose administered and a reduction in increase of dose through the life of the inhaler using inhalers according to the invention.

EXAMPLE 2

The EOU interior valve deposition and dosing profile on valves was investigated with PTFE/acetal polymer metering chambers. Fluticasone Propionate/Propellant HFA134a Inhalers, 50 microgram, 120 actuation were manufactured using the DF60 valve and DF60 valve modified with 5%PTFE/acetal in the metering chamber. The inhalers were stored for a minimum of 2 weeks before analysis. The deposition and dosing data are presented in Tables 3 and 4.

TABLE 3

EOU Interior Valve Drug Deposition

| Valve type | Amount of fluticasone propionate deposited (mg) |
|---|---|
| Standard Valve | 0.44 |
| Valve modified with 5% PTFE/acetal | 0.32 |

The valve according to the invention demonstrates significantly lower interior valve deposition than that seen in the standard valve. This is due to the 5%PTFE/acetal polymer metering chamber having fluorine at the surface.

TABLE 4

Dosing Data

| Valve type | Beginning of Use Dose (mcg) | | End of Use Dose (mcg) | | Increase in dose during life of inhaler (mcg) |
|---|---|---|---|---|---|
| | Mean | SD (%) | Mean | SD (%) | |
| Standard Valve | 40.5 | 4.1 | 53.0 | 7.6 | 12.5 |
| Modified Valve | 42.6 | 2.2 | 51.4 | 7.1 | 8.8 |

Several experiments were conducted to investigate the quantity of drug deposited on different types of polymer blocks.

The following method was used to analyse the quantity of drug deposited on the polymer blocks for each experiment. Firstly, the fluticasone propionate suspension was evacuated quickly by piercing the MDI can. The valve was then cut from the MDI and the polymer block carefully removed for washing. The polymer block was washed quantitatively with acetonitrile into a 50 ml volumetric flask containing 25 ml water. The drug solution was made to volume and the resultant solution assayed for fluticasone propionate by HPLC.

EXAMPLE 3

The effect of different polymers on the quantity of drug deposited was investigated. The polymer blocks used had the standard injection moulded finish. The polymer blocks were cut to an appropriate size to fit an 8 ml-inhaler can. The polymer blocks were then placed into MDI containing a suspension of 0.35% w/w fluticasone propionate in 12 g of propellant HFA134a. The inhalers were stored for a minimum of 2 weeks before analysis of the drug deposited on the polymer blocks. The data are presented in Tables 5 and 6.

TABLE 5

Effect of Polymer Used on Drug Deposition

| Polymer Used | Amount of fluticasone propionate deposited (mg) |
|---|---|
| Acetal | 0.23 |
| Hostaform C9021TF (20% PTFE/acetal blend) | 0.15 |
| THV200G (TFE, HFP, vinylidene fluoride) | 0.14 |
| THV500G (TFE, HFP, vinylidene fluoride) | 0.09 |
| PFA6515N (perfluoroalkoxy) | 0.05 |
| FEP6107 (fluorinated ethylenepropylene) | 0.04 |
| ETFE ET6125 (ethylenetetrafluoroethylene) | 0.04 |

TABLE 6

Effect of Polymer Used on Drug Deposition

| Polymer Used | Amount of fluticasone propionate deposited (mg) |
|---|---|
| Polyester | 0.70 |
| Polyester/PTFE (LNP WL4040) | 0.49 |

The addition of PTFE to polyester reduces the fluticasone deposition significantly compared to pure polyester.

The lowest levels of drug deposition are seen with the polymers with the greater levels of fluorination (PFA, ETFE, and FEP).

EXAMPLE 4

The effect of fluorine coating the polymer and the quantity of drug deposited was investigated. Acetal was the polymer coated with fluorine. The coating process was the conventionally known plasma coating process.

The polymer blocks were cut to an appropriate size to fit an 8 ml-inhaler can. The polymer blocks were then placed into MDI containing a suspension of 0.34% w/w fluticasone propionate in 12 g of propellant HFA134a. The inhalers were stored for a minimum of 2 weeks before analysis of the drug deposited on the polymer blocks. The data are present in Table 7.

TABLE 7

Effect of Fluorine Coating on Drug Deposition

| Polymer Used | Amount of fluticasone propionate deposited (mg) |
|---|---|
| Acetal | 0.70 |
| CF4 plasma coating/acetal | 0.33 |

Fluorinating the surface of the acetal by coating has reduced the drug deposition significantly compared to acetal which does not have a fluorinated coating.

It will be understood that the present disclosure is for the purpose of illustration only and the invention extends to modifications, variations and improvements thereto which will be within the ordinary skill of the person skilled in the art.

What is claimed is:

1. A valve for an aerosol container, comprising:
   a valve body including a metering chamber having a first internal surface and a transfer passage in liquid communication with said metering chamber; and
   an actuator having a dispensing passage in liquid communication with said metering chamber, said dispensing passage having a second internal surface, wherein at least said valve body comprises a mixture of a first fluorinated polymer and a non-fluoridated polymer and said first internal surface includes a plasma coated second fluorinated polymer.

2. The valve of claim 1, wherein said mixture includes at least one material selected from the group consisting of a polyacetal, a polyester, a silicone, a polytetrafluoroethylene, a polyethylenetetrafluoroethylene, a polyvinyldienefluoride, a polyperfluoroalkoxyalkane, a polyvinylfluoride, a polychlorotrifluoroethylene, a fluorinated polyethylene propylene, a copolymer of a polytetrafluoroethylene and a polyperfluoroalkoxyalkane, a copolymer of a polytetrafluoroethylene and a polyhexafluoropropylene, a copolymer of a polyvinyldienefluoride and a polyhexafluoropropylene, a copolymer of a polytetrafluoroethylene and a polyperfluoro (propyl vinyl ether); a blend of a polytetrafluoroethylene, a polyhexafluoropropylene, and a polyvinylidene fluoride, blends thereof and combinations thereof.

3. The valve of claim 2, wherein said first fluorinated polymer is selected from the group consisting of polytetrafluoroethylene, a polyvinylfluoride and a polychlorotrifluoroethylene.

4. The valve of claim 1, wherein said valve body includes a sampling chamber in liquid communication with said transfer passage.

5. The valve of claim 4, wherein said valve body further includes a radial passage and said actuator includes an inner canal.

6. The valve of claim 5, wherein said valve body further includes an orifice in liquid communication with said sampling chamber.

7. The valve of claim 1, wherein said valve is adapted to dispense a medicament suspended in a suitable propellant.

8. The valve of claim 7, wherein said propellant is substantially free of excipients.

9. The valve of claim 7, wherein said medicament is selected from the group consisting of fluticasone propionate, salbutamol, beclomethasone dipropionate, salmeterol, (-)-4-amino-3,5-dichloro-α(((6-(2-(pyridinyl)ethoxy) hexyl) amino)methyl)benzenemethanol, pharmaceutically acceptable salts, solvates or esters thereof, and combinations thereof.

10. The valve of claim 9, wherein said medicament includes fluticasone propionate and salmeterol.

11. The valve of claim 9, Wherein said medicament comprises fluticasone propionate.

12. The valve of claim 9, wherein said medicament comprises salmeterol.

13. The valve of claim 9, wherein said medicament comprises beclomethasone dipropionate.

14. The valve of claim 9, wherein said medicament comprises fluticasone propionate and said propellant comprises $CF_3CH_2F$.

15. The valve of claim 7, wherein said medicament comprises a particulate having an inhalation effective particle size, and wherein said medicament is present in said propellant in a therapeutically effective concentration.

16. The valve of claim 15, wherein said particle size is less than approximately 20 microns and said concentration is in the range of approximately 0.0005 to 10% by weight.

17. The valve of claim 15, wherein said particle size is in the range of approximately 1 to 10 microns and said concentration is in the range of approximately 0.0005 to 5% by weight.

18. The valve of claim 15, wherein said particle size is in the range of approximately 1 to 5 microns and said concentration is in the range of 0.01 to 1.0% by weight.

19. The valve of claim 7, wherein said propellant includes an excipient selected from the group consisting of a suitable solvent, a suitable co-solvent, a suitable surfactant and combinations thereof.

20. The valve of claim 7, wherein said propellant is selected from the group consisting of $CF_3CH_2F$, $CF_3CHFCF_3$ and combinations thereof.

21. The valve of claim 7, wherein said propellant is selected from the group consisting of a $C_1$ to $C_4$ hydrogen-containing chlorofluorocarbon, a $C_1$ to $C_4$ hydrogen-containing fluorocarbon, a $C_1$ to $C_4$ perfluorocarbon and combinations thereof.

22. The valve of claim 21, wherein said $C_1$ to $C_4$ hydrogen-containing chlorofluorocarbon is selected from the group consisting of $CH_2ClF$, $CClF_2CHClF$, $CF_3CHClF$, $CHF_2CClF_2$, $CF_3CH_2Cl$, and $CClF_2CH_3$.

23. The valve of claim 21, wherein said $C_1$ to $C_4$ hydrogen-containing fluorocarbon is selected from the group consisting of $CHF_2CHF_2$, $CF_3CH_2F$, $CHF_2CH_3$, and $CF_3CHFCF_3$.

24. The valve of claim 21, wherein said $C_1$ to $C_4$ perfluorocarbon is selected from the group consisting of $CF_3CF_3$ and $CF_3CF_2CF_3$.

25. The valve of claim 21, wherein said propellant is selected from the group consisting of $CHClF_2$, $CH_2F_2$, and $CF_3CH_3$.

26. The valve of claim 1, wherein said mixture includes up to 80% by weight of said first fluorinated polymer.

27. The valve of claim 1, wherein said mixture includes up to 40% by weight of said first fluorinated polymer.

28. The valve of claim 1, wherein said mixture includes up to 20% by weight of said first fluorinated polymer.

29. The valve of claim 1, wherein said mixture includes up to 5% by weight of said first fluorinated polymer.

30. The valve of claim 1, wherein said mixture comprises approximately 5% by weight of a polytetrafluoroethylene and approximately 95% by weight of a polyacetal.

31. The valve of claim 1, wherein said mixture comprises 20% by weight of a polytetrafluoroethylene and 80% by weight a polyacetal.

32. The valve of claim 1, wherein said mixture comprises a polytetrafluoroethylene and a polyester.

33. The valve of claim 1, wherein said mixture comprises a polytetrafluoroethylene, a polyester and a silicone.

34. The valve of claim 1, wherein said actuator comprises a mixture of said first fluorinated polymer and said non-fluorinated polymer, and wherein said second internal surface includes a plasma coated second fluorinated polymer.

35. A metering valve made by a process comprising the steps of:

providing a valve body comprising a mixture of a fluorinated polymer and a non-fluorinated polymer, said valve body including a metering chamber having a first interior surface, and a transfer passage in liquid communication with the metering chamber;

providing an actuator having a dispensing passage in liquid communication with said metering chamber, said dispensing passage having a second internal surface; and plasma reacting a suitable fluorocarbon monomer on at least said interior surface of said metering chamber.

36. The valve of claim 34, wherein said mixture includes at least one material selected from the group consisting of a polyacetal, a polyester, a stainless steel, a silicone, a polytetrafluoroethylene, a polyethylenetetrafluoroethylene, a polyvinyldienefluoride, a polyperfluoroalkoxyalkane, a polyvinylfluoride, a polychlorotrifluoroethylene, a fluorinated polyethylene propylene, a copolymer of a polytetrafluoroethylene and a polyperfluoroalkoxyalkane, a copolymer of a polytetrafluoroethylene and a polyhexafluoropropylene, a copolymer of a polyvinyldienefluoride and a polyhexafluoropropylene, a copolymer of a polytetrafluoroethylene and a polyperfluoro(propyl vinyl ether); a blend of a polytetrafluoroethylene, a polyhexafluoropropylene, and a polyvinylidene fluoride, blends thereof and combinations thereof.

37. The valve of claim 35, wherein said fluorocarbon monomer comprises $CF_4$.

38. The valve of claim 35, wherein said step of reacting said suitable fluorocarbon monomer comprises a plasma coating process.

39. The valve of claim 35, wherein said actuator comprises a mixture of said first fluorinated polymer and said non-fluorinated polymer, and wherein said second internal surface includes a plasma coated second fluorinated polymer.

40. The valve of claim 39, including the step of plasma coating said second internal surface of said actuator with a second fluorinated polymer.

\* \* \* \* \*